United States Patent [19]

Coyne et al.

[11] 4,072,421
[45] Feb. 7, 1978

[54] METHOD AND APPARATUS FOR OPTICAL DISCRIMINATION OF PARTICLES

[75] Inventors: Lawrence J. Coyne, White Plains; Wilberdan V. George, Brooklyn; Warren Groner, Whitestone, all of N.Y.

[73] Assignee: Technicon Instruments Corporation, Tarrytown, N.Y.

[21] Appl. No.: 718,745

[22] Filed: Aug. 30, 1976

[51] Int. Cl.² .................. G01N 33/16; G01N 21/26
[52] U.S. Cl. .................. 356/39; 250/222 PC; 356/103; 356/201
[58] Field of Search .................. 356/39–42, 356/102–104, 201, 204–205, 207–208; 324/71 CP; 350/87, 89, 17; 23/230 B; 250/222 PC, 573; 235/92 PC

[56] References Cited

U.S. PATENT DOCUMENTS

| | | | |
|---|---|---|---|
| 2,850,230 | 9/1958 | Polanyi et al. | 355/39 |
| 3,046,837 | 7/1962 | Barabas et al. | 350/89 |
| 3,740,143 | 6/1973 | Groner et al. | 356/39 |
| 3,781,112 | 12/1973 | Groner et al. | 356/39 |
| 3,947,123 | 3/1976 | Carlson et al. | 356/39 |

OTHER PUBLICATIONS

Mondal, P. K. "Nomenclature of an Image Forming System" applied Optics, 10–1975, p. 2319.
Loveland, R. P. "Photomicrography", John Wiley & Sons, 1970, p. 415.

*Primary Examiner*—John K. Corbin
*Assistant Examiner*—Wm. H. Punter
*Attorney, Agent, or Firm*—S. P. Tedesco

[57] ABSTRACT

Method and apparatus for improved optical discrimination in a total particle population of particles having a significant light absorption characteristic and particles having a significant light scattering characteristic. There is provided in such a method a combination of steps including, directing a beam of light from a source to transversely illuminate at an optical interaction station particles passed one by one through such station, partially obstructing the beam beyond the station for passage of scattered and unscattered portions of the beam, when a particle is in said beam and detecting one of said beam portions.

20 Claims, 5 Drawing Figures

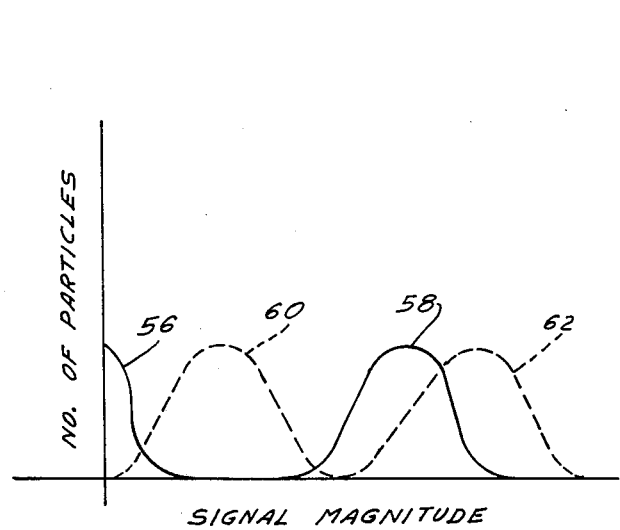
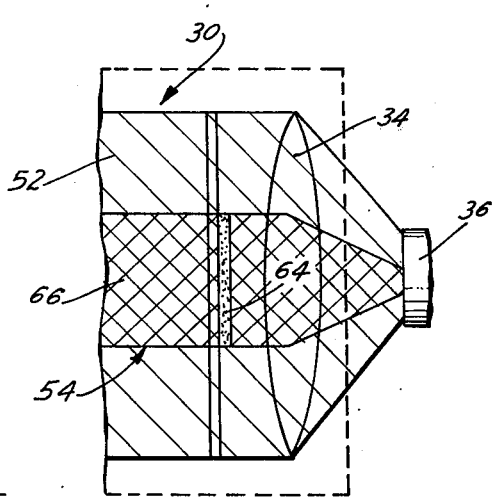
FIG. 2
FIG. 3
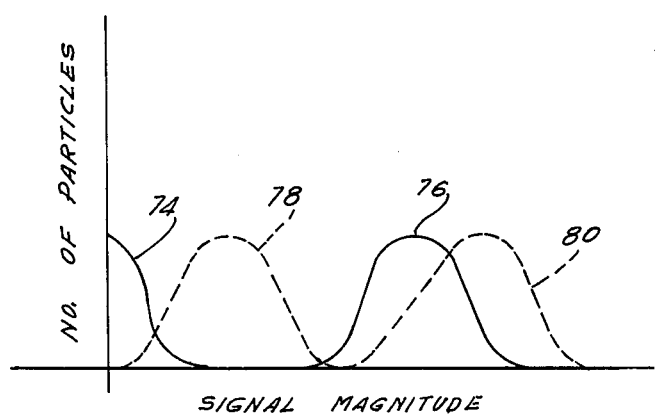
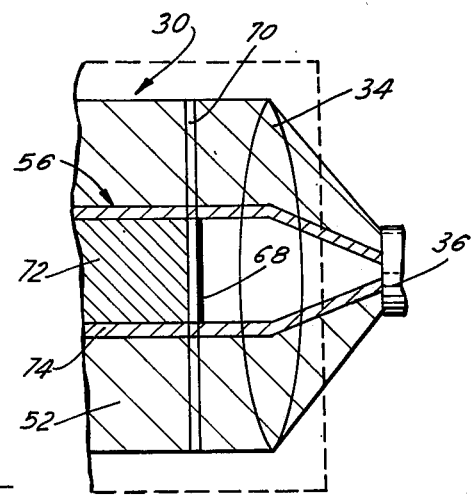
FIG. 5
FIG. 4

METHOD AND APPARATUS FOR OPTICAL DISCRIMINATION OF PARTICLES

It is known that in the classification of particles, having the characteristic of scattering light forwardly, a subclass of a total population of such particles may be discriminated, as for the purpose of counting the particles of such subclass, wherein the last-mentioned particles have a significant light absorption characteristic. For example, Groner et al U.S. Pat. No. 3,740,143 describes the discrimination for counting purposes of at least one class of leukocytes, e.g., eosinophils, in an aliquot of a whole blood sample within a total population of leukocytes. For this purpose, the cytoplasm of the eosinophils are stained by a conventional dye to give the eosinophils a significant light absorption characteristic by which they may be discriminated by an optical interaction from the remainder of the leukocytes.

In accordance with the teaching of that patent, the eosinophils of the sample aliquot are discriminated for counting purposes in an optical channel detecting absorption of the eosinophils as the leukocytes of that aliquot pass one by one through an illumination beam. Simultaneously, both eosinophils and the other leukocytes of that aliquot are detected in a reference optical channel by light scatter, i.e., light gain, for counting a total leukocyte population.

It is also known, as described in Groner et al. U.S. Pat. No. 3,781,112, that a subclass of leukocytes, treated with a similar dye or stain so as to have a significant absorption characteristic, may be discriminated within a total leukocyte population by utilizing two optical channels both of which simultaneously detect light scatter or light gain by the transverse passage of leukocytes one by one through an illumination beam. In that technique, a stained leukocyte is discriminated by an increase in light scatter at a non-absorbing wavelength in one channel and a simultaneous decrease in light scatter at an absorbing wavelength in the other channel. The total leukocyte population is counted utilizing light scatter in the channel in which light gain is detected at the non-absorbing wavelength.

It is desired to enhance the sensitivity of such particle discrimination, particularly with reference to lightly stained particles. Further, it is desired to improve by optics, rather than by relatively expensive electrical signal processing, the discrimination of populations of stained and unstained particles. The present invention contemplates such improvements.

One object of the invention is to provide an improved method and apparatus for optical discrimination in a total particle population of particles having a significant light absorption characteristic and particles having a significant light scattering characteristic. Another object is to provide in such a method a combination of steps including, directing a beam of light from a source to transversely illuminate at an optical interaction station particles passed one by one through such station, and partially obstructing the beam beyond the station for passage of scattered and unscattered portions of the beam toward a photodetector.

In the drawings:

FIG. 2 is a diagram illustrating pulse height analysis of particle populations showing improved separation of such populations in the use of the apparatus of FIG. 1;

FIG. 3 is a fragmentary view, similar to FIG. 1, illustrating a modified form of the apparatus;

FIG. 4 is a fragmentary view, similar to FIG. 3, illustrating another modified form of the apparatus; and FIG. 5 is a view, similar to FIG. 2, illustrating improved separation of particle populations in the use of the apparatus of FIG. 4.

Figure 1:
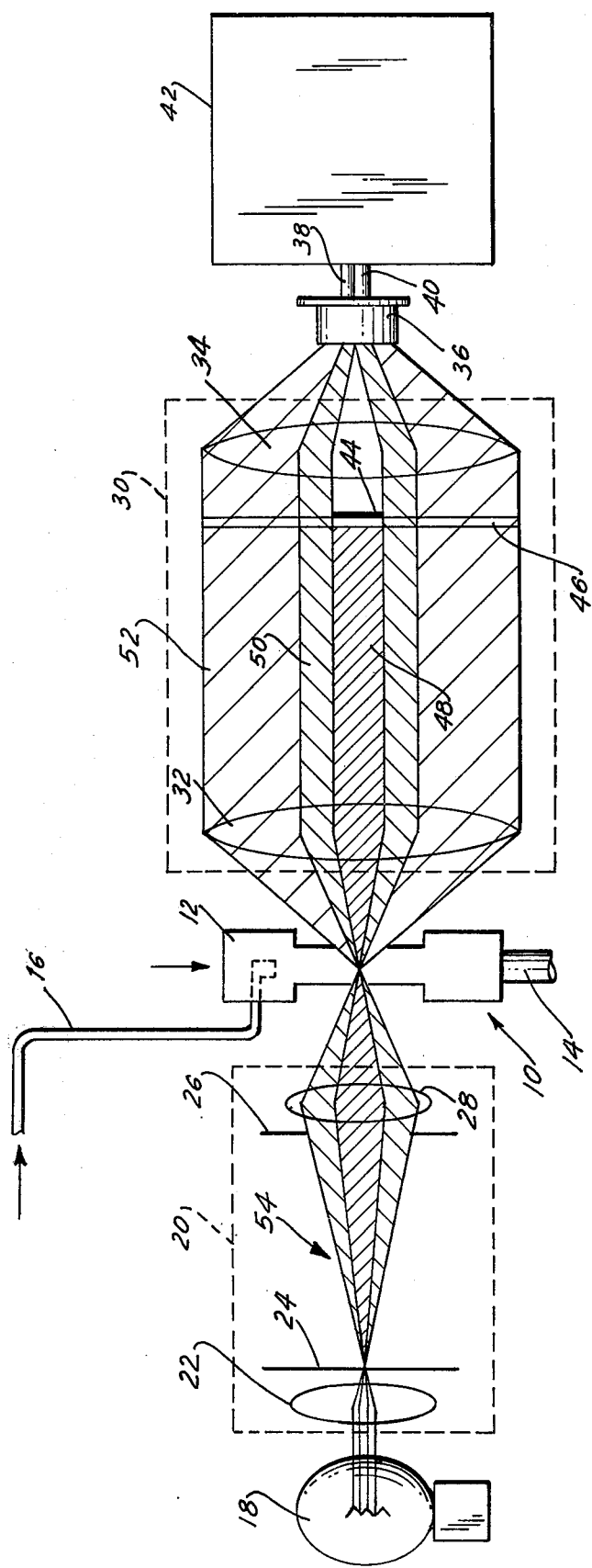
FIG. 1 is a somewhat diagramatic view of an optical system embodying the invention.

In FIG. 1, there is illustrated by way of example an optical system for discrimination, within a particle population, of a subclass of particles. The particle population may take the form of leukocytes of a sample of whole blood and the subclass of particles may take the form of any type of leukocytes in the nuclei or cytoplasm of which a stain may be precipitated in a staining reaction. The system includes an optical chamber 10, shown as a flow cell, hereinafter referred to as an optical interaction station. Leukocytes of the sample are caused to flow one after another in a sheathed stream through the station 10 in the direction indicated by the arrow. The liquid for the sheath, which may be water, is supplied through conduit 12 in the direction indicated by the arrow. The leukocytes of the whole blood sample are in suspension and those of the class of interest have been selectively stained in a conventional manner, not shown, prior to analysis so that the other leukocytes in the sample remain unaltered or unstained. The leukocytes of interest may be the class of eosinophils, for example. The sample flows from a nonillustrated source through a conduit 16. The sheath stream may be supplied from any nonillustrated source for entrainment of the cellular particles. The combined stream is discharged to waste through an outlet 14 downstream of the station 10.

As the particles or cells pass through the optical interaction station 10, they pass one by one through a narrow transverse beam of light directed from a light source 18 which may be a tungsten-halogen lamp. The illumination lens system may be of the illustrated Kohler type. The illustrated illumination lens system indicated generally at 20, includes condensing lens 22, aperture masks 24,26 and a projection lens 28. By way of example, the dimension of the illumination beam defined by mask 26 may be 0.140 in. and the N.A. of the system 20 may be approximately 0.11. Further, the cross-section of the optical interaction station 10 illuminated by the beam may be approximately 20 microns by 100 microns.

Beyond the optical interaction station 10, there is provided an optical detection lens system, indicated generally at 30, which is illustrated as including an objective lens 32 and a detector lens 34, which detector lens collects light for impingement on a photodetector 36 which may be of the silicon type. The detection lens system 30 may have an N.A. of approximately 0.25. The photodetector 36 is shown having leads 38,40 coupled to a conventional counting system 42 for counting particles as in pulse height analysis. The counting system 42 may include a conventional nonillustrated count display. The optical system of FIG. 1 thus far described may be considered a typical one-channel system for discrimination of stained and unstained particles or leukoctyes by light absorption or light loss detected by the photodetector 36 as the leukocytes pass one by one through the optical interaction station 10. With the addition to the optical detection system 30 of an opaque light stop of the same cross-sectional dimension or larger than the cross-sectional dimension of the illumination beam in the last-mentioned system, the optical system of FIG. 1 would be considered a typical one-channel system for discrimination of stained and unstained particles by light scatter or light gain detected by the photodetector 36 as the particles or cells pass one by one through the station 10.

It is known that unstained particles or leukocytes scatter more light than stained leukocytes at an absorbing wavelength, and that, while unstained cells exhibit some light absorbance, this absorbance is less than the light absorbance of stained cells as detected at an absorbing wavelength. Generally, unstained particles or leukocytes have an unaltered light absorbance characteristic, while stained particles or leukocytes have an altered absorbance characteristic. Further, it is known that when forwardly scattering particles such as leukocytes are illuminated, as described above, some light is scattered without the entrance aperture of the optical detection system, resulting in nonspecific light loss within such detection system, also referred to as pseudo-absorption. Such nonspecific light loss when detected as by a photodetector results in a signal which indicates more light absorption of stained and unstained particles, particularly unstained partles, than is actually absorbed. This has heretofore made discrimination of populations of stained and unstained particles sometimes troublesome, particularly with reference to lightly stained particles. We have found that such nonspecific light loss or pseudo-absorption may be minimized in an optical channel such as described above with added features described hereinafter.

In the optical system of FIG. 1, the photodetector is sensitive to light absorbance of particles such as leukocytes passing through the station 10, as described above. A partial obstruction 44 obstructs a region of the illumination beam intermediate the station 10 and the photodetector 36 and is located preferably in the plane wherein the lens 32 forms an image of lens 28. The particular obstruction 44 is supported as on a planar, transparent glass plate 46 and may be of any symetrical outline such as of annular or cruciform shape, for example. The obstruction 44 of FIG. 1, which is not wavelength sensitive as herein defined, is shown as an opaque substance conventionally deposited on the plate 46 and may be of disc shape. The obstruction 44 in this form blocks the entire central portion 48 of the illumination beam in the lens system 30. In this form, an outer annular portion 50 of the illumination beam passes the obstruction 44 for impingement on the photodetector 36. Thus, it will be evident that the obstruction 44 does not block light, such as scattered light, in the area 52 surrounding the illumination beam and within the light collection capacity of the lens 34 which focuses such light on the photodetector 36.

It will be observed that with this optical configuration, the obstruction 44 reduces the light incident on the photodetector 36 when no particle or cell is present in the illumination beam. Hence, when an unstained cell moves into the beam, indicated generally at 54, at the optical interaction station 10, light rays of the beam 54 formerly blocked by the obstruction 44 scatter photons forwardly into the areas 50,52 within the optical detection system 30 for collection and impingement on the photodetector 36. This compensates for nonspecific light loss or pseudo-absorption caused by photons being scattered without the entrance aperture of the optical detection system 30 by such a particle entering the illumination beam. Thus, the magnitude of the signal generated by a photodetector 36 is reduced from what it would have been without the presence in the system of the obstruction 44. The foregoing applies to a lesser extent to the entrance into the illumination beam 54 of a stained cell which, as previously noted, scatters less light and has a significant absorption characteristic. The ratio of light loss of stained cells to light loss of unstained cells, as detected by the photodetector 36, is increased. This results in improved separation and discrimination in pulse height analysis of populations of stained and unstained cells as represented in FIG. 2.

In FIG. 2, the results of the last-mentioned analysis according to the invention is approximated wherein the solid line curves 56,58 represent the total sample populations of unstained and stained cells, respectively. Further, in this view, the results of such pulse height analysis utilizing a prior art optical system is approximated wherein the broken line curves 60,62 represent the sample populations of unstained and stained cells, respectively. FIG. 2 graphically represents the improved separation and discrimination of stained and unstained cell populations according to the invention. No attempt has been made in FIG. 2 to represent the relative sizes of the aforementioned populations.

In the particular apparatus previously described with reference to optical dimensions, it was found that a partial obstruction of the opaque type such as the obstruction 44 of the beam 54 should obstruct approximately 8–15% of the beam when the apparatus is utilized as described for analysis of leukocytes. In this environment, it was found that the optimum cross-sectional dimension of the obstruction was approximately 0.025 in.

The optimum size of the obstruction 44 is determined by such factors as the angular parameters of the particular optical system selected for such examination. Generally, as the size of a given type of particle is increased, a greater proportion of light is scattered by such a particle in the forward direction. One may essentially determine the magnitude of light scattered forwardly without, or outside of, the optical detection system 30, i.e., the entrance angle or aperture of the lens 32, by the particles of interest and then essentially determine the size of the partial obstruction 44 based on the magnitude of light scatter past the obstruction within the system 30, so that these magnitudes are substantially equal. The greater the amount of forward light scatter without the entrance angle of the lens 32, the greater the amount of light scatter past the partial obstruction within the lens system 30. In this manner, the partial obstruction compensates for light scattered without the system 30.

While not illustrated, the single-channel optical system of FIG. 1 for the determination of light absorption may be advantageously combined with one or more optical channels of the type described in Groner et al U.S. Pat. No. 3,740,143, as in substitution for one or more light absorption channels described therein and each associated or combined with a channel for light scatter determinations for analysis or counting of particles of cells of stained and unstained types. Such a combination has the advantage of keying the particles of a particular subclass to the total particle population.

In the modified form of the apparatus shown in FIG. 3, the opaque obstruction 44 is replaced by a partial obstruction 64 in the form of a neutral density filter which, in this case, extends throughout the cross-sectional area 66 of the illumination beam comprised of both areas 48,50 of the form of FIG. 1. The filter or obstruction 64 may be supported in any convenient manner as from a planar, transparent plate similar to the plate 46. The obstruction 64 transmits therethrough only a portion of the illumination beam 54, and light scatter may pass around the obstruction 64 in the light collection zone 52 of the optical detection system 30, as in the form of FIG. 1. The operation of the form of FIG. 3 is similar to that described with reference to the form of FIG. 1 concerning the discrimination and separation of stained and unstained particles.

A partial obstruction, rather than the conventional full obstruction of the illumination beam, may be employed to advantage in an optical channel similar to FIG. 1 but which, instead of detecting light absorption or loss from particles entering the illumination beam, detects light scatter or gain from such particles. Such an optical channel, shown in FIG. 4, may be substituted for the optical channel designated channel I in Groner et al U.S. Pat. No. 3,781,112, for example. In accordance with that patent, as previously noted, a stained leukocyte is distinguished or discriminated in an illumination beam by a decrease in light scatter detected by a photodetector sensitive to an absorbing wavelength in Channel I and a simultaneous increase in light scatter by the particle in the beam detected by a photodetector more sensitive to a wavelength other than an absorption wavelength in a channel designated Channel II. The disclosure of U.S. Pat. No. 3,781,112 is incorporated herein by reference.

The modified form of FIG. 4 is similar to the form of FIG. 1. As shown in FIG. 4, a partial obstruction 68 may obstruct a significantly greater portion of the light beam 54 than the previously described obstruction 44. In an optical system of the previously described dimensions, the obstruction 68, which may be structured, located and supported in the manner of the previously described obstructions including that of FIG. 3, may obstruct approximately 15–25% of the illumination beam. The obstruction 68 may be opaque and of disc form supported in similar manner to the obstruction 44 on a transparent plate 70 similar to the plate 46. As shown in FIG. 4, a portion 72 of the illumination beam is blocked by the obstruction 68 and a portion 74 of the beam passing around the obstruction 68 is focused by the detection lens 34 on the absorption-sensitive photodetector 36, together with any scattered light in the area 52 within the collection capacity of the lens 34. It will be appreciated from the foregoing that, when there is no particle or leukocyte present in the illumination beam 54, the portion 74 of the beam is incident on the photodetector 36. This light level is substantially higher than would be the case, essentially zero, with the beam fully obstructed. Hence, when a stained cell, which scatters less light than an unstained cell, enters the illumination beam, the resultant light gain or scatter detected by the photodetector 36 is substantially less than would be the case with the beam fully obstructed according to conventional practice. To a lesser extent, the same is true when an unstained cell enters the illumination beam 54. The ratio of light gained from unstained cells to light gain from stained cells is increased as evident in FIG. 5, similar to FIG. 2, representing pulse height analysis of stained and unstained cell populations utilizing the apparatus of FIG. 4. This results in improved separation and discrimination of these populations.

In FIG. 5, the results of the last-mentioned analysis are approximated wherein the solid line curves 74,76 represent the sample populations of stained and unstained cells, respectively. Further, in this view, the results of such pulse height analysis utilizing a prior art optical system is approximated wherein the broken line curves 78,80 represent the sample populations of stained and unstained cells, respectively. FIG. 5 graphically represents the improved separation and discrimination of stained and unstained cell populations achieved with the apparatus of FIG. 4.

While several forms of the invention have been illustrated and described, it will be apparent, especially to those versed in the art, that the method and apparatus for optical discrimination of particles may take other forms and is susceptible to various changes in details without departing from the principles of the invention.

What is claimed is:

1. Apparatus for discriminating particles having particular light absorbing and scattering characteristics when illuminated by a beam of light, comprising: means for passing said particles, in turn, along an optical interaction station, a light source for directing a beam of light transversely through said station along an optical axis, and an optical detection system having an entrance aperture and including a photodetector for receiving light as scattered and absorbed by particles being passed, in turn, through said station, said detection system including means intermediate said station and said photodetector for partially obstructing an interior portion of said light beam while passing to said photodetector a portion of said scattered light which is substantially equal to the light which is scattered by said particles, in turn, outside said entrance aperture.

2. Apparatus as defined in claim 1, wherein: said means partially obstructing said beam comprises an opaque element.

3. Apparatus as defined in claim 1, wherein: said means partially obstructing said beam comprises a neutral density filter.

4. Apparatus as defined in claim 3, wherein: said neutral density filter extends throughout the cross-sectional dimension of said beam.

5. Apparatus as defined in claim 1, wherein: said means partially obstructing said beam obstructs between substantially 8–15% of said beam.

6. Apparatus as defined in claim 1, wherein: said means partially obstructing said beam obstructs between substantially 15–25% of said beam.

7. Apparatus as defined in claim 1, whrein: said photodetector is wavelength sensitive.

8. Apparatus as defined in claim 1, wherein: said particles comprise a stained class of leukocytes, and said photodetector detects light loss at an absorbing wavelength.

9. Apparatus as defined in claim 8, wherein: said support means comprises a conduit for the flow of leukocytes contained in a sheathed stream through said station.

10. Apparatus as defined in claim 8, further including an optical illumination lens system intermediate said source and said station, said system directing said beam and including as the final lens a projection lens, said optical detection system including objective and detector lenses, said means partially obstructing said beam being in the plane wherein said objective lens forms an image of said projection lens.

11. Apparatus as defined in claim 1, wherein: said particles comprise stained leukocytes, and said photodetector detects light gain at an absorbing wavelength.

12. Apparatus as defined in claim 1, wherein: said opaque element is of disc form.

13. Apparatus as defined in claim 1, wherein: said particles are stained and unstained leukocytes.

14. A method for discriminating particles having a particular light absorbing and light scattering characteristics when illuminated by a beam of light, comprising the steps of: passing said particles, in turn, along an optical interaction station, directing a beam of light from a light source transversely through said station along an optical axis, detecting light passed through said station as scattered and absorbed by each particle, in turn, by an optical detection system having an entrance aperture and a photodetector disposed along said optical axis, and partially obstructing an interior portion of said light beam passing to said photodetector at a location intermediate said station and said photodetector by an amount substantially equal to the light scattered by said particles, in turn, outside said entrance aperture.

15. A method as defined in claim 14, wherein: said obstructing of said beam is by totally occluding a portion of said beam.

16. A method as defined in claim 14, wherein: said detecting of said beam is wavelength sensitive.

17. A method as defined in claim 14, wherein: said particles comprise a stained class of leukocytes, said detection being of light gain at an absorbing wavelength.

18. A method as defined in claim 14, wherein: said particles comprise a stained class of leukocytes, said detection being of light loss at an absorbing wavelength.

19. A method as defined in claim 18, wherein: said passing of said particles one by one through said beam is by flowing said particles in a sheathed stream.

20. A method as defined in claim 19, wherein: said particles are stained and unstained leukocytes.

* * * * *